United States Patent
Heydrich et al.

(10) Patent No.: US 8,282,793 B2
(45) Date of Patent: Oct. 9, 2012

(54) CONTINUOUS PROCESS FOR PREPARING NERAL IN PURE OR ENRICHED FORM

(75) Inventors: Gunnar Heydrich, Limburgerhof (DE); Nawid Kashani-Shirazi, Ilvesheim (DE); Christoph Jäkel, Limburgerhof (DE); Joachim Schmidt-Leithoff, Mannheim (DE)

(73) Assignee: BASF SE, Ludwigshafen (DE)

( * ) Notice: Subject to any disclaimer, the term of this patent is extended or adjusted under 35 U.S.C. 154(b) by 169 days.

(21) Appl. No.: 12/666,478

(22) PCT Filed: Jun. 9, 2008

(86) PCT No.: PCT/EP2008/057164
§ 371 (c)(1),
(2), (4) Date: Dec. 23, 2009

(87) PCT Pub. No.: WO2009/000634
PCT Pub. Date: Dec. 31, 2008

(65) Prior Publication Data
US 2010/0193348 A1 Aug. 5, 2010

(30) Foreign Application Priority Data
Jun. 26, 2007 (EP) .................................. 07111080

(51) Int. Cl.
*B01D 3/00* (2006.01)
(52) U.S. Cl. .................. 203/71; 203/99; 568/420
(58) Field of Classification Search .................. 203/71, 203/99; 568/420
See application file for complete search history.

(56) References Cited

U.S. PATENT DOCUMENTS

| 2,471,134 | A | | 5/1949 | Wright |
| 2,895,886 | A | * | 7/1959 | Schneider .................. 202/158 |
| 4,230,533 | A | | 10/1980 | Giroux |
| 5,094,720 | A | * | 3/1992 | Sasser .......................... 203/6 |
| 5,507,356 | A | * | 4/1996 | Roth et al. .................. 165/111 |
| 5,785,819 | A | | 7/1998 | Kaibel et al. |
| 6,175,044 | B1 | | 1/2001 | Therre et al. |

FOREIGN PATENT DOCUMENTS

| CA | 1242309 A1 | 9/1988 |
| DE | 3522234 A1 | 1/1987 |
| DE | 10223971 A1 | 12/2003 |
| DE | 10223974 A1 | 12/2003 |
| DE | 10330934 A1 | 2/2005 |
| EP | 122367 A2 | 10/1984 |
| EP | 126288 A2 | 11/1984 |
| EP | 133510 B1 | 2/1985 |

(Continued)

OTHER PUBLICATIONS

Kaibel, "Distillation columns with vertical partitions," Chem. Eng. Technol., 1987, vol. 10, pp. 92-98.

(Continued)

*Primary Examiner* — Robert A Hopkins
(74) *Attorney, Agent, or Firm* — Connolly Bove Lodge & Hutz LLP

(57) ABSTRACT

The present invention relates to a continuous process for preparing neral (cis-citral) in pure or enriched form by distillatively separating neral from substance mixtures comprising essentially neral and geranial (trans-citral). This distillative separation is performed in a dividing wall column or in a connection of two distillation columns in the form of a thermal coupling.

17 Claims, 2 Drawing Sheets

FOREIGN PATENT DOCUMENTS

| EP | 640367 | B1 | 3/1995 |
|---|---|---|---|
| EP | 780147 | B1 | 6/1997 |
| EP | 992477 | A1 | 4/2000 |
| EP | 1514955 | B1 | 3/2005 |

OTHER PUBLICATIONS

Knott, "Distillation's great leap forward," Process Engineering, 1993, vol. 74, No. 2, pp. 33-34.

Lestak, et al., "Heat transfer across the wall of dividing wall columns," Trans IChemE, 1994, vol. 72, Issue A, pp. 639-644.

Lestak, et al., "Advanced distillation saves energy & capital," Chemical Engineering, 1997, vol. 104, No. 7, pp. 72-76.

U.S. Appl. No. 12/677,688, filed Mar. 11, 2010, Heydrich et al.

Kaibel, et al., "Gestaltung destillativer trennungen unter einbeziehung thermodynamischer gesichtspunkte," Chem.-Ing.-Tech., 1989, vol. 61, No. 1, pp. 16-25.

Kaibel, et al., "Thermodynamics-guideline for the development of distillation column arrangements," Gas Separation & Purification, 1990, vol. 4, pp. 109-144.

Wolff, et al., Operation of integrated three-product (petlyuk) distillation columns, Ind. Eng. Chem. Res., 1995, vol. 34, pp. 2094-2103.

* cited by examiner

CONTINUOUS PROCESS FOR PREPARING NERAL IN PURE OR ENRICHED FORM

CROSS-REFERENCE TO RELATED APPLICATIONS

This application is a national stage application (under 35 U.S.C. §371) of PCT/EP2008/057164, filed Jun. 9, 2008, which claims benefit of European application 07111080.3, filed Jun. 26, 2007.

BACKGROUND OF THE INVENTION

The present invention relates to a continuous process for preparing neral (cis-citral) in pure or enriched form by distillatively separating neral from substance mixtures comprising essentially neral and geranial (trans-citral). This distillative separation is performed in a dividing wall column or in a connection of two distillation columns in the form of a thermal coupling.

Citral (3,7-dimethylocta-2,6-dienal) is an important aroma chemical and the starting material or intermediate for preparation of a wide variety of materials of value and active ingredients. It is especially significant in this context that citral is an α,β-unsaturated aldehyde which, on the one hand, is attractive as a synthesis unit, but, on the other hand, also tends to side reactions, for example to isomerizations, owing to its high reactivity. Citral can either be isolated from natural sources or prepared synthetically, and is typically obtained in the form of mixtures of the E/Z isomers neral and geranial. For specific applications in the field of aroma or synthesis chemistry, it may be desirable to be able to use the two double bond isomers mentioned in pure or enriched form.

A problem is that the geranial and neral compounds for use in very substantially pure form differ only by the configuration of the ethylenic double bond conjugated to the particular aldehyde group and can be interconverted easily by thermal isomerization thereof. As a result, the efficient separation of geranial- and neral-containing mixtures on the industrial scale is a technical problem which still has not been solved satisfactorily.

EP 1 514 955 relates to a process for distillative workup of the electrolysis output of the electrochemical oxidation of 1,1,2,2-tetramethoxyethane with methanol to give trimethyl orthoformate in a liquid electrolyte, wherein a dividing wall column having from 30 to 150 theoretical plates is used.

DE 103 30 934 discloses a process for continuously isolating citronellal or citronellol from a crude mixture comprising at least one of these compounds by rectification. Preference is given to using those starting mixtures which are obtained by partial hydrogenation of citral and/or citronellal.

DE 102 23974 relates to a process for continuously isolating two stereoisomeric isoprenoid alcohols, specifically nerol and geraniol, from a crude mixture by rectification, the crude mixture being introduced into the side of a feed column, at least one draw column coupled to the feed column being provided and a first and a second isoprenoid alcohol being drawn off from the draw column. The feed column and the draw column are coupled such that there is no cross-mixing of vapor and condensate at least in the region of the draw of the isoprenoid alcohols.

DE 102 23 971 discloses a process for continuously isolating an α,β-unsaturated aldehyde, specifically citral from a crude mixture comprising it, by rectification. The crude mixture is introduced into the side of a feed column with a rectifying section above the feed point and a stripping section below the feed point, an upper combining column which communicates with the upper end of the rectifying section and has a condenser at the upper end of the column, and a combining column which communicates with the lower end of the stripping section and has a heater at the lower end of the column provided and a combining column which communicates with the upper combining column and the lower combining column. The α,β-unsaturated aldehyde is drawn off from the draw column as a side draw, and lower-boiling compounds are drawn off at the top of the upper combining column and higher-boiling compounds at the bottom of the lower combining column.

None of the documents cited describes the separation of stereoisomeric α,β-unsaturated aldehydes. Compared to the stereoisomeric α,β-unsaturated alcohols specified in DE 102 23 974, these have an increased reactivity, specifically easier isomerizability. DE 102 23971 likewise does not disclose a separation of stereoisomeric α,β-unsaturated aldehydes, but rather merely the separation of a mixture of cis- and trans-citral from other chemical compounds.

Proceeding from this prior art, it was an object of the present invention to provide a process for preparing very substantially pure or enriched neral (cis-citral) proceeding from inexpensively available citral. The process should be performable with a low level of apparatus complexity, in an economically viable manner and on the industrial scale, while leading especially only to a low degree of formation of decomposition products and by-products, i.e. should afford the desired product in high purity and in maximum yield.

BRIEF SUMMARY OF THE INVENTION

The object is surprisingly achieved in accordance with the invention by the provision of a continuous process for preparing neral of the formula (I)

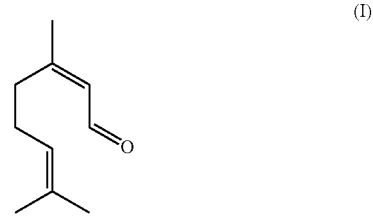

in pure or enriched form by distillative separation of neral from substance mixtures comprising neral and geranial of the formula (II)

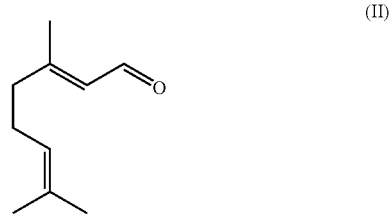

wherein the distillative separation is performed in a dividing wall column or in a connection of two distillation columns in the form of a thermal coupling with from 80 to 200 theoretical plates and one or more side draws at an absolute operating pressure of from 5 to 200 mbar.

A BRIEF DESCRIPTION OF THE FIGURES

DETAILED DESCRIPTION OF THE INVENTION

Figure 1:
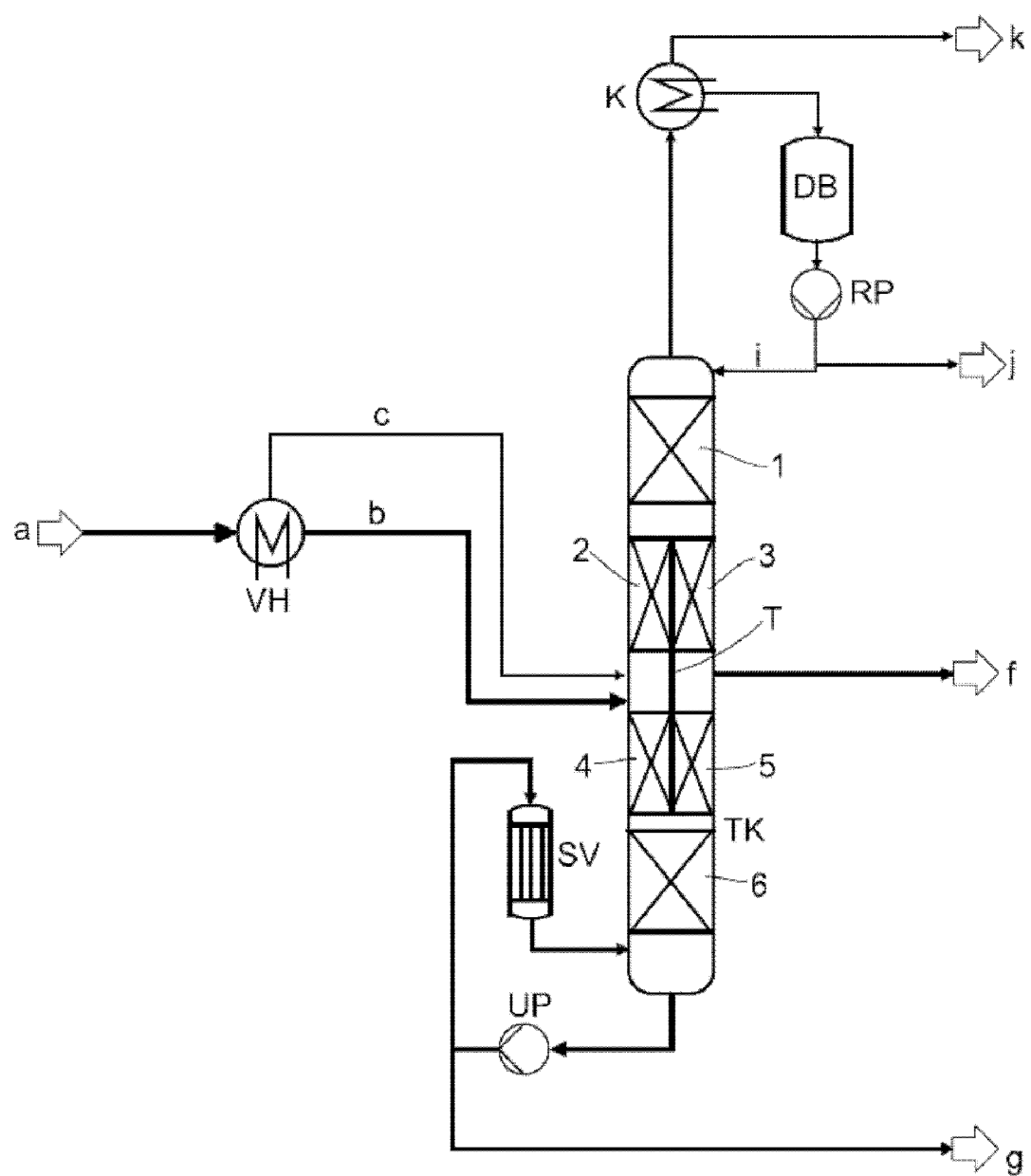
FIG. 1 shows a schematic of a preferred embodiment of the inventive separation of the neral- and geranial-comprising substance mixture to be used into a low-neral top fraction (j), a high-neral side fraction (f) and a low-neral bottom fraction (g). The neral- and geranial-containing feed to the dividing wall column may be in liquid form (b) in gaseous form (c), or in gaseous and liquid form.

In a preferred embodiment, the inventive distillative separation of neral is performed in a dividing wall column having from 80 to 200 theoretical plates and one or more side draw points at an absolute operating pressure of from 5 to 200 mbar.

Suitable feedstocks for performing the process according to the invention are substance mixtures which comprise neral and geranial, preferably those which consist predominantly of the double bond isomers neral and geranial. Among these, preference is given to those substance mixtures which comprise from 90% by weight to 100% by weight, more preferably from 95 to 98% by weight (based in each case on the total amount of the particular substance mixture) of geranial and neral, or consist thereof in the proportions specified, and may additionally comprise to a minor degree, i.e. in a proportion of up to 10% by weight, preferably of up to 5% by weight (based in each case on the total amount of the particular substance mixture), of further components, for example isomers, by-products or impurities. A preferred feedstock is synthetic citral, especially that which has been obtained by thermal cleavage of 3-methyl-2-buten-1-al diprenyl acetal with elimination of prenol to give cis/trans-prenyl (3-methyl-butadienyl) ether, Claisen rearrangement thereof to give 2,4,4-trimethyl-3-formyl-1,5-hexadiene and subsequent Cope rearrangement thereof, as described, for example, in EP 0 992 477. This comprises typically from about 45 to about 55% by weight of neral in addition to from about 55 to about 45% by weight and from about 1 to 5% by weight of further compounds or impurities.

In a preferred embodiment of the process according to the invention, a substance mixture is used which comprises from 30 to 70% by weight, preferably from 40 to 60% by weight, of neral, from 70 to 30% by weight, preferably from 60 to 40% by weight, of geranial and from 0 to 5% by weight of further components where the percentages must add up to 100% by weight.

The inventive distillative separation typically performed in such a way that the substance mixture comprising neral and geranial used is separated into in each case one or more low boiler, medium boiler and high boiler fraction(s) and neral is withdrawn in pure or enriched form as a medium boiler fraction at the side draw of the dividing wall column used, or of the connection of two distillation columns in the form of a thermal coupling, in liquid or gaseous form.

The process according to the invention is accordingly also a continuous process for isolating neral, preferably a continuous process for isolating neral in pure or enriched form by distillative separation of neral from substance mixtures comprising neral and geranial, wherein the distillative separation is undertaken in a dividing wall column or in a connection of two distillation columns in the form of a thermal coupling with from 80 to 200 theoretical plates and one or more side draws at an absolute operating pressure, i.e. at an absolute pressure in the dividing wall column or the connection of two distillation columns in the form of a thermal coupling, of from 5 to 200 mbar, preferably from 5 to 100 mbar.

The dividing wall column to be used in accordance with the invention, or the connection of two distillation columns in the form of a thermal coupling, has from 80 to 200, preferably from 100 to 180 theoretical plates and one or more, preferably from 1 to 5, more preferably 1 to 3, and most preferably 1 or 2, side draws. Preference is given in accordance with the invention to using a dividing wall column as described above.

The process according to the invention is performed at an absolute operating pressure in the dividing wall column or in the connection of two distillation columns in the form of a thermal coupling of from 5 to 200 mbar, preferably from 5 to 100 mbar, more preferably from 5 to 70 mbar, most preferably from 10 to 50 mbar and especially preferably from 10 to 40 mbar. Preference is given to operating the dividing wall column or the connection of two distillation columns in the form of a thermal coupling such that the absolute top pressure is from 10 to 50 mbar, preferably from 10 to 40 mbar. Likewise preferably, the dividing wall column or the connection of two distillation columns in the form of a thermal coupling is operated such that the absolute bottom pressure is from 5 to 200 mbar, preferably from 10 to 100 and more preferably from 20 to 50 mbar.

In the performance of the process according to the invention, the reflux ratio can be varied within wide limits and is typically from about 5:1 to about 2000:1, preferably from about 20:1 to 1000:1. Also advantageous is a dephlegmator mode, i.e. only the reflux is condensed in the top condenser of the column and fed back to the column. In such an energetically favorable case of partial condensation, the top product to be discharged is obtained exclusively in the downstream cooler, which can be operated at lower temperature.

The term "neral in enriched form" is understood to mean neral-containing substance mixtures which have a higher content of neral than the particular substance mixture comprising neral or geranial used in accordance with the invention. The term "neral in enriched form" is preferably understood to mean neral which has a purity, i.e. a neral content, of from 80 to 95% by weight, preferably from 85 to 95% by weight and more preferably from 90 to 95% by weight (based in each case on the total amount). The process according to the invention also enables the preparation of neral (cis-citral) in pure form. The term "neral in pure form" is understood to mean neral having a content of greater than or equal to 95, 96 or 97% by weight, preferably greater than or equal to 98% by weight and more preferably from 98 to 99.5% by weight.

The term "neral in pure form" is especially preferably understood to mean neral which has a geranial content of up to 1% by weight preferably from 0.05 to 0.5% by weight and more preferably from 0.1 to 0.3% by weight. Likewise preferably, the neral in pure form obtainable in accordance with the invention has a content of isocitrals of the formulae (III), (IV) and (V)

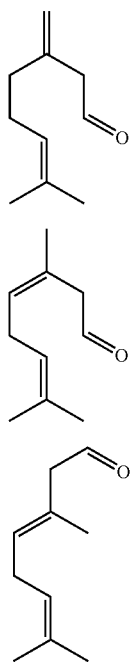

(III)

(IV)

(V)

of up to 2% by weight, preferably from 0.1 to 1% by weight, all data in the context of the present invention being based on the total amount of the particular substance mixtures.

The feed, i.e. the substance mixture to be used, can be conducted in liquid or gaseous form into the dividing wall column or the connection of two distillation columns in the form of a thermal coupling, preferably into the dividing wall column, and separated there into a top fraction and bottom fraction, and one or more side outputs, preferably in a plurality of side outputs as described above. In one side output the neral product of value is obtained in the desired purity. In a particular embodiment, a post condenser is connected downstream of the top condenser of the column and is cooled with cooling liquid (for example brine), and in which a low-neral low-boiler fraction is also obtained.

For the continuous distillative separation of multi-substance mixtures, according to the prior art, various process variants are in common use. In the simplest case, the feed mixture is separated into two fractions, a low-boiling top fraction and a high-boiling bottom fraction. In the case of separation of feed mixtures into more than two fractions, according to this process variant, a plurality of distillation columns have to be used. In order to limit the apparatus complexity, in the separation of multi-substance mixtures, if possible, columns with liquid or vaporous side draws are used. However, the possible uses of distillation columns with side draws are greatly limited by the fact that the products withdrawn at the side draws are never entirely pure. In the case of side draws in the rectifying section, which are typically effected in liquid form, the side product still comprises fractions of low-boiling components, which have to be removed via the top. The same applies to side draws in the stripping section, which are usually effected in vaporous form, in the case of which the side product still comprises high boiler fractions. The use of conventional side draw columns is therefore limited to cases in which contaminated side products are permissible.

One means of remedy is that of dividing wall columns. This column type is described, for example in U.S. Pat. No. 2,471, 134; U.S. Pat. No. 4,230,533; EP 0 122 367; EP 0 126 288; EP 0 133 510; Chem. Eng. Technol. 10 (1987) 92-98; Chem.-Ing.-Tech. 61 (1989) No. 1, 16-25; Gas Separation and Purification 4 (1990) 109-114; Process Engineering 2 (1993) 33-34; Trans IChemE 72 (1994) Part A 639-644 and Chemical Engineering 7 (1997) 72-76.

In the case of this design, it is likewise possible to withdraw side products in pure form. In the middle region above and below the feed point and the side draw is mounted a dividing wall which seals the feed section from the withdrawal section and prevents cross-mixing of liquid and vapor streams within this column section. In the separation of multi-substance mixtures, this reduces the number of distillation columns required in total. Since this column type constitutes an apparatus simplification of thermally coupled distillation columns, it additionally has a particularly low energy consumption. A description of thermally coupled distillation columns, which can be designed in various apparatus configurations, can likewise be found in the abovementioned references in the technical literature. Dividing wall columns and thermally coupled columns offer advantages over the arrangement of conventional distillation columns both with regard to energy demand and to capital costs, and are therefore increasingly being used industrially.

FIG. 1 shows a schematic of a preferred embodiment of the inventive separation of the neral- and geranial-comprising substance mixture to be used into a low-neral top fraction (j), a high-neral side fraction (f) and a low-neral bottom fraction (g). The neral- and geranial-containing feed to the dividing wall column may be in liquid form (b) in gaseous form (c), or in gaseous and liquid form.

Figure 2:
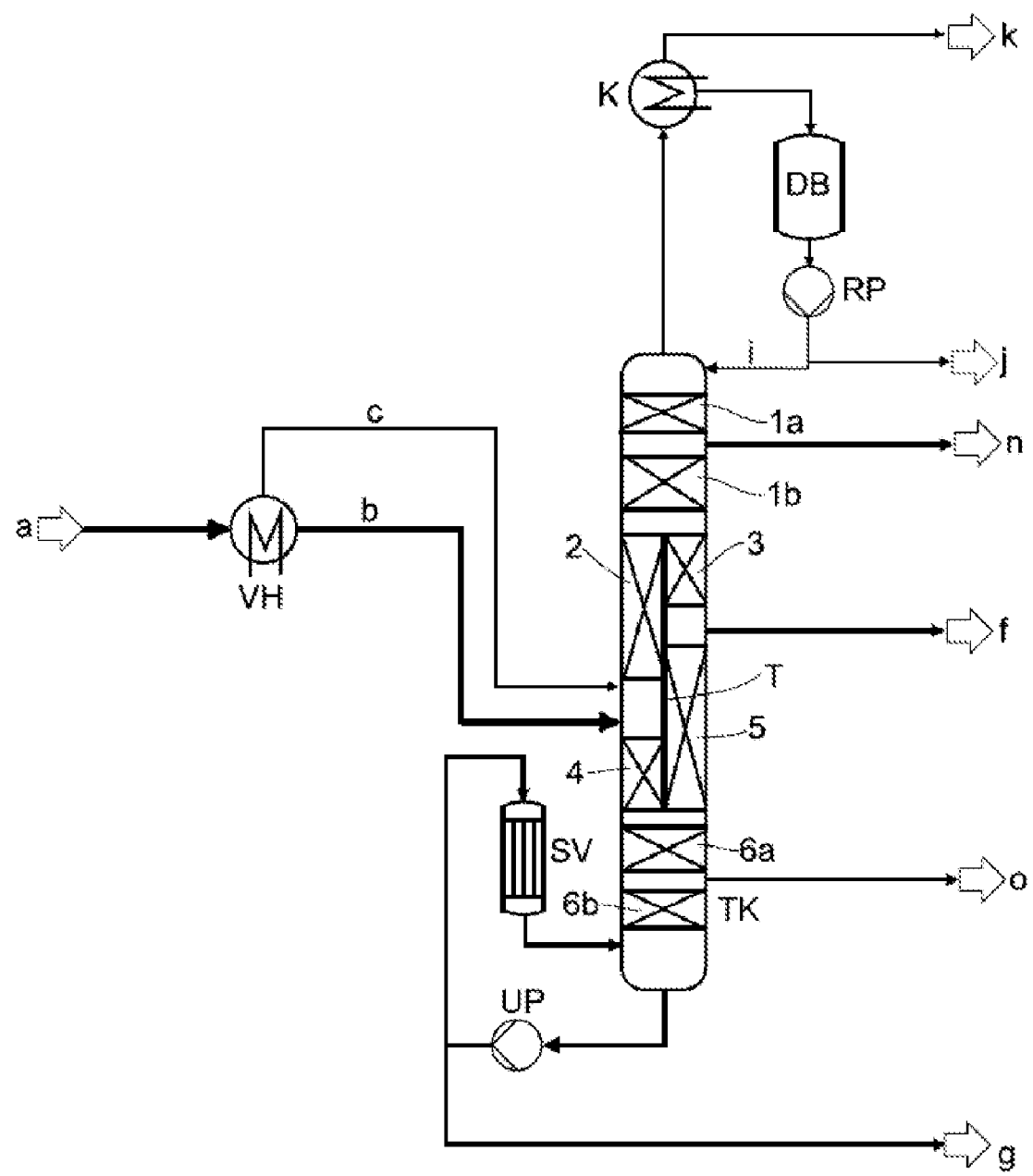
FIG. 2 shows a schematic of a particularly preferred embodiment of the process according to the invention for preparing neral in pure or enriched form, in which, in addition to the features including the side draw (f) specified under FIG. 1, the side draw points (n) and (o) are provided.

FIG. 2 shows a schematic of a particularly preferred embodiment of the process according to the invention for preparing neral in pure or enriched form, in which, in addition to the features including the side draw (f) specified under FIG. 1, the side draw points (n) and (o) are provided.

The process according to the invention is performed continuously. Accordingly, the neral- and geranial-comprising substance mixtures for use as the starting material are fed continuously to the dividing wall column or to the connection of two distillation columns in the form of a thermal coupling, and the products (fractions) obtained in accordance with the invention and/or by-products are discharged continuously.

A further condenser is typically connected downstream of the column, and has a working temperature from 10 to 40 K, preferably from 20 to 30 K, below the working temperature of the top condenser of the dividing wall column. With the aid of this, a majority of the low boilers still present in the top stream (k) can be precipitated.

Dividing wall columns can also be replaced by two thermally coupled columns in each case. This is favorable in particular when the columns are already present or the columns are to be operated at different pressures. In the case of thermally coupled columns, it may be advantageous to evaporate the bottom stream of the first column partially or completely in an additional evaporator and then to feed it to the second column. This preliminary evaporation is an option especially when the bottom stream of the first column comprises relatively large amounts of medium boilers. In this case, the preliminary evaporation can be effected at a lower temperature level and the evaporator of the second column can be deburdened. In addition, this measure allows the stripping section of the second column to be significantly deburdened. The preliminarily evaporated stream can be fed to the second column in biphasic form or in the form of two separate streams.

In addition, both in the case of dividing wall columns and in the case of thermally coupled columns, it may be advantageous to subject the feed stream to a preliminary evaporation and then to feed it to the column in biphasic form or in the form of two streams. This preliminary evaporation is an option particularly when the feed stream comprises relatively large amounts of low boilers. The preliminary evaporation allows the stripping section of the column to be significantly deburdened.

Dividing wall columns and thermally coupled columns can be designed either as packed columns with random packings or structured packings, or as tray columns. In the process according to the invention for preparing neral in pure or enriched form, packed columns are used. In this case, structured sheet metal or fabric packings with a specific surface area of from about 100 to 750 $m^2/m^3$, preferably from about 350 to 500 $m^2/m^3$ are particularly suitable.

If, as in the case of the present invention, particularly high demands are made on the purities of the products, it is favorable to equip the dividing wall with thermal insulation. A description of the different means of thermal insulation of the dividing wall can be found in EP-A 0 640 367. A double-wall design with an intermediate narrow gas space is particularly favorable.

For the regulation of dividing wall columns and thermally coupled columns, various regulation strategies have been described. Descriptions can be found in U.S. Pat. No. 4,230,533; DE 35 22 234; EP 0 780 147; Process Engineering 2 (1993) 33-34 and Ind. Eng. Chem. Res. 34 (1995), 2094-2103.

In the separation of multi-substance mixtures into a low boiler fraction, medium boiler fraction, and high boiler fraction, there typically exist specifications regarding the maximum permissible proportion of low boilers and high boilers in the medium boiler fraction. In this case, either individual components critical for the separation problem, known as key components, or the total of several key components is specified. In the context of the present invention, these key components are geranial as the high-boiling secondary component and isocitral or a mixture of isomeric isocitrals as the low-boiling secondary component.

The compliance with the specification for the high boilers in the medium boiler fraction can be regulated, for example, via the division ratio of the liquid at the upper end of the dividing wall. The division ratio of the liquid at the upper end of the dividing wall is preferably adjusted such that the concentration of the key components for the high boiler fraction in the liquid at the upper end of the dividing wall makes up from 10 to 80%, preferably from 30 to 50%, of the value which is to be achieved in the side draw product. The liquid division is preferably adjusted to the effect that more liquid is passed to the feed section in the event of higher contents of key components of the high boiler fraction, and less in the case of lower contents of key components of the high boiler fraction.

Accordingly, the specification for the low boilers in the medium boiler fraction can be regulated by means of the heating power. For example, the heating power in the evaporator is adjusted such that the concentration of key components of the low boiler fraction in the liquid at the lower end of the dividing wall makes up from 10 to 80%, preferably from 30 to 50% of the value to be achieved in the side draw product. The heating power is preferably adjusted to the effect that the heating power is increased in the event of a higher content of key components of the low boiler fraction, and the heating power is reduced in the event of a lower content of key components of the low boiler fraction.

To compensate for disruption in the feed rate or the feed concentration, it has additionally been found to be advantageous to ensure, through an appropriate regulation mechanism (for example through regulation rules in the process control system that the flow rates of the liquids to the column parts (2), i.e. the rectifying section of the feed section, and (5), i.e. the stripping section of the withdrawal section, cannot fall below 30% of their normal value.

Suitable devices for the withdrawal and division of the liquids at the upper end of the dividing wall and at the side draw(s) are collecting spaces for the liquid arranged both internally and outside the column, which assume the function of a pump reservoir or ensure a sufficiently high static liquid head, which enable further conduction of liquid regulated by control units, for example valves. In the case of use of packed columns the liquid is first captured in collectors and passed from there into an internal or external collecting space.

Instead of a dividing wall column—which is preferable with regard to capital costs in the case of new construction—it is also possible to connect two distillation columns in the manner of a thermal coupling such that they correspond to a dividing wall column with regard to the energy demand. In the case of availability of existing columns, they may be a viable alternative to dividing wall columns. The most suitable forms of the connection can be selected according to the number of plates of the columns available.

When, in this embodiment of the process according to the invention, two distillation columns are used in a connection in the form of a thermal coupling, it has been found to be advantageous to equip both distillation columns thermally coupled in this way with a dedicated evaporator and condenser. In addition, the two thermally coupled columns can be operated at different pressures and only liquids can be conveyed into the connecting streams between the two columns. In a preferred embodiment, the bottom stream of the first column is evaporated partially or completely in an additional evaporator and then fed to the second column in biphasic form or in the form of a gaseous stream and a liquid stream.

In a particularly preferred embodiment the process according to the invention is performed in a plant as shown schematically in FIG. 1. In the preferred embodiment a dividing wall column (TK) is used, which has a dividing wall (T) in the longitudinal direction of the column to form an upper combined column region (1), a lower combined column region (6), a feed section (2, 4) with rectifying section (2) and stripping section (4) and a withdrawal section (3, 5) with stripping section (3) and rectifying section (5).

The substance mixture (a) which comprises neral and geranial and serves as the feedstock is, in accordance with the invention, preferably fed into the middle region of the feed section (2, 4), the neral is obtained in pure or enriched form as a side draw (f) from the middle region of the withdrawal section (3, 5) and one or more low boiler fractions are removed from the upper combined column region (1) and one or more high boiler fractions from the lower combined column region (6).

The feed stream (a) can be introduced into the column (TK) via a preheater (VH) as a liquid (b), gaseous (c) or partly liquid and partly gaseous stream. The top stream of the column is condensed completely or partially in the condenser (K). In the case of partial condensation (dephlegmator operation) the offgas stream (k) of the top condenser (K) typically still comprises noticeable amounts of condensable low boilers which can then be condensed in a post condenser operated at low temperature.

The top product condensed in the condenser (K) can be buffered in the distillate vessel (DB) and recycled back to the column as column reflux (i) via the reflux pump (RP). If required, a distillate fraction (j) can also be obtained therefrom. In the case of integration of the condenser into the top of the column, the distillate vessel (DB) and the reflux pump (RP) can be dispensed with.

The bottom stream is advantageously fed via the circulation pump (UP) to the bottom evaporator (SV), which is preferably configured as a falling-film evaporator. The bottom effluent (g) of the column (TK) can also be withdrawn from this pumped circulation stream.

The product of value, neral in pure or enriched form, is preferably drawn off as a liquid side draw, stream (f), from the withdrawal section of the dividing wall column (TK). It is also possible to withdraw the product of value stream (f) as a gaseous draw if required, but in that case a further condenser is typically required.

The upper combined subregion (1) of the column has typically from 5 to 50%, the rectifying section (2) of the feed section of the column from 5 to 50%, the stripping section (4) of the feed section of the column from 2 to 50%, the stripping section (2) of the withdrawal section of the column from 5 to 50%, the rectifying section (5) of the withdrawal section from 2 to 50%, and the lower combined section (6) of the column from 5 to 50%, of the total number of theoretical plates of the column, where the percentages selected add up to 100%.

Preferably, the upper combined subregion (1) of the column has from 10 to 25%, the rectifying section (2) of the feed section of the column from 15 to 30%, the stripping section (4) of the feed section of the column from 5 to 20%, the stripping section (2) of the withdrawal section of the column from 15 to 30%, the rectifying section (5) of the withdrawal section from 5 to 20%, and the lower combined section (6) of the column from 10 to 25% of the total number of theoretical plates of the column, where the percentages selected must add up to 100%.

The sum of the number of theoretical plates of the subregions (2) and (4) in the feed section is preferably from 80 to 110%, more preferably from 95 to 105%, of the sum of the number of plates of subregions (3) and (5).

Advantageously, the feed point and the side draw point, with regard to the position of the theoretical plates, are arranged at different heights in the column, by virtue of the feed point being arranged from 1 to 50, preferably from 30 to 45, theoretical plates higher or lower than the side draw point.

It has additionally been found to be advantageous when the subregion of the column divided by the dividing wall, consisting of subregions (2), (3), (4) and (5) or parts thereof, is equipped with structured packings or random packings (preferably fabric packings such as Montz A3-500, Sulzer BX or CY). It has additionally been found to be advantageous when the dividing wall is configured with thermal insulation in these subregions.

The vapor stream at the lower end of the dividing wall can be adjusted through the selection and/or dimensions of the separating internals and/or the incorporation of devices which generate a pressure drop, for example of perforated plates, such that the ratio of the vapor stream in the feed section to that of the withdrawal section is from 0.8 to 1.2, preferably from 0.9 to 1.1.

The liquid effluxing from the upper combined subregion (1) of the column is advantageously collected in a collecting space arranged within the column or outside the column and divided in a controlled manner by a fixed or regulable setting at the upper end of the dividing wall such that the ratio of the liquid stream to the feed section relative to that to the withdrawal section is from 0.1 to 2.0 in the case of a principally liquid feed and from 1.0 to 2 in the case of a gaseous feed. Preference is given in accordance with the invention to a liquid feed.

The liquid effluxing from the upper combined subregion (1) to the feed section can be delivered by means of a pump or introduced under quantitative control by means of a static feed head of at least 1 m, preferably by means of closed-loop control in conjunction with the liquid level control of the collecting space. The control is preferably adjusted such that the amount of liquid introduced to the feed section cannot fall below 30% of the desired normal value. In addition, the division of the liquid effluxing from the subregion (3) in the withdrawal section of the column to the side draw and to the subregion (5) in the withdrawal section of the column is advantageously adjusted by closed-loop control such that the amount of liquid applied to the subregion (5) cannot fall below a magnitude of 30% of the desired normal value. The normal value should advantageously be assumed to be from two to four times the amount, based on the feed rate of geranial/neral mixture.

The dividing wall column preferably has, at the upper and lower end of the dividing wall, sampling means samples can be taken in liquid or gaseous form from the column continuously or at time intervals and can be analyzed for their composition, preferably by gas chromatography.

The division ratio of the liquid at the upper end of the dividing wall is preferably adjusted such that the concentration of those components of the high boiler fraction for which a particular limiting value for the concentration is to be achieved in the side draw (especially geranial), in the liquid at the upper end of the dividing wall amounts to from 10 to 80%, preferably from 30 to 50%, of the value which is to be achieved in the side draw product. The liquid division should preferably be adjusted to the effect that more liquid is passed to the feed section in the case of higher contents of components of the high boiler fraction and less in the case of lower contents of components of the high boiler fraction.

The heating power in the evaporator (SV) is preferably adjusted such that the concentration of those components of the low boiler fraction for which a particular limiting value for the concentration is to be achieved in the side draw (especially isocitrals), at the lower end of the dividing wall amounts to from 10 to 80%, preferably from 30 to 50%, of the value which is to be achieved in the side draw product. The heating power is advantageously adjusted to the effect that the heating power is increased in the case of a higher content of components of the low boiler fraction and the heating power is reduced in the case of a lower content of components of the low boiler fraction.

The distillate is withdrawn, i.e, the low-boiling by-products are withdrawn, preferably under temperature control. The control temperature used is advantageously a measurement point in the subregion (1) of the column, which is arranged from 3 to 8, preferably from 4 to 6, theoretical plates below the upper end of the column.

The bottom product is preferably withdrawn under quantitative control, preferably depending on the feed rate.

The neral process product obtained as the side product in pure or enriched form is preferably withdrawn under level control, the control parameter used preferably being the liquid level in the column bottom.

The feed stream (a) is preferably partially or completely pre-evaporated and fed to the column in biphasic form or in the form of a gaseous and a liquid stream.

In a preferred embodiment, a dividing wall column is used, whose dividing wall is not welded into the column but rather is configured in the form of loosely inserted and appropriately sealed subsegments.

The liquid division in the individual subregions of the column can preferably be adjusted in a controlled inhomogeneous manner, in which case the liquid is introduced to an enhanced degree in the wall region especially in subregions (2) and (5), and the liquid is introduced to a reduced extent in the wall region in subregions (3) and (4).

The division ratio of the refluxing liquid between withdrawal and feed side of the dividing wall is preferably from about 1:1 to about 3:1, preferably from about 1:1 to about 1.5:1.

The position of the dividing wall in the individual subregions of the column can advantageously be adjusted such that the cross sections of feed section and withdrawal section have different areas.

In a particularly preferred embodiment of the process according to the invention, at least one low boiler fraction is obtained as a liquid or gaseous side draw, preferably as a liquid side draw (n) in the upper section (1) of the column, preferably from 4 to 10 theoretical plates below the top of the column (see FIG. 2). In this case, it is appropriate to divide the upper column section (1) into two sections ((1a) and (1b)). Between these sections, a suitable collector collects the liquid effluxing from section (1a) and distributes it again to the section (1b) below (see FIG. 2). A fraction which is low in low boilers and low in neral can be drawn off from the collector, said fraction comprising isomeric citrals in particular.

These isocitral-rich by-product fractions obtainable through the additional side draw (n) can be utilized further in a suitable manner; for example, it can be subjected to a thorough hydrogenation or to a partial hydrogenation to tetrahydrogeraniol, which allows waste products or by-products for disposal to be avoided.

An embodiment particularly preferred in accordance with the invention therefore relates to a continuous process for preparing neral of the formula (I) in pure or enriched form by distillative separation of neral from substance mixtures comprising neral and geranial of the formula (II), the distillative removal being performed in a dividing wall column (TK) which has a dividing wall (T) in the longitudinal direction of the column to form an upper combined column region (1), a lower combined column region (6), a feed section (2, 4) with rectifying section (2) and stripping section (4), and a withdrawal section (3, 5) with stripping section (3) and rectifying section (5), having from 80 to 200 theoretical plates and a plurality of, preferably from 2 to 4, more preferably 2 or 3, side draw points at an absolute operating pressure of from 5 to 200 mbar, and neral being obtained in pure or enriched form as a side draw (f) from the middle region of the withdrawal section (3, 5) and a low boiler fraction (n) being obtained as a liquid or gaseous side draw, preferably as a liquid side draw, from the upper combined column region (1).

In a further preferred embodiment of the process according to the invention, at least one high boiler fraction is obtained as a gaseous side draw (o) in the lower combined subregion of the column (6), preferably from 1 to 5 theoretical plates above the bottom of the column (see FIG. 2). This allows a geranial-rich product which is particularly low in high boilers to be obtained. In this case, it may be appropriate to divide the lower column section (6) into two sections (6a and 6b).

Between these sections, a suitable collector collects the liquid effluxing from section (6a) and distributes it again to the section (6b) below (see FIG. 2), and withdraws the gas stream for the side draw.

The bottom, evaporator (SV) used for the dividing wall column may advantageously be a thin-film apparatus, for example a falling-film evaporator.

The top condenser (K) may be configured, for example, as a plate apparatus and be integrated into the column jacket.

The neral obtainable in accordance with the invention in pure or enriched form is obtained continuously via the side draw, or, in the case that further side draws are provided, via the middle side draw (f), and has, in a preferred embodiment, a neral content of more than 98% by weight, preferably from 98.5 to 99.5% by weight, a geranial content of less than 0.3% by weight and a content of other isomers (citral isomers of the formulae (III), (IV) and (V)) of less than 1% by weight (based in each case on the total amount of mixture obtained), possibly in addition to small amounts of further impurities.

When an upper side draw (n) as described above is provided, it is possible there to obtain a by-product mixture which typically has a neral content of less than 80% by weight, a geranial content of less than 0.1% by weight and a content of other isomers, especially of the citral isomers of the formulae (III), (IV) and (V) of more than 20% by weight, preferably of more than 30% by weight. In addition, in a lower side draw (o) which is provided if desired, just like in the bottom fraction (g), a product mixture with a neral content of less than 20% by weight and a geranial content of more than 70% by weight can be obtained. The top fraction (j) typically has a neral content of less than 30% by weight. The low boiler fraction (k) removed therefrom typically has a neral content of less than 5% by weight in addition to isocitrals as the main components.

The present invention also relates to the use of a dividing wall column as described above or of a connection of two distillation columns in the form of a thermal coupling, preferably of a dividing wall column with from 80 to 200 theoretical plates and one or more side draw points, for continuous preparation of neral of the formula (I) in pure or enriched form by distillative separation of neral from substance mixtures comprising neral and geranial of the formula (II) and to the use thereof for isolating neral. The present invention additionally also relates to a dividing wall column as described above or a connection of two distillation columns in the form of a thermal coupling, preferably to a dividing wall column having from 80 to 200 theoretical plates and one or more side draw points, which is suitable for continuous preparation of neral of the formula (I) in pure or enriched form by distillative separation of neral from substance mixtures comprising neral and geranial of the formula (II).

The examples which follow serve to illustrate the invention without restricting it in any way:

Example 1

The dividing wall column used for the examples which follow was constructed from five glass sections each of length 1.2 m and of internal diameter 64 mm. A dividing wall made of sheet metal was inserted into the three middle sections. Laboratory packings (Sulzer CY) were installed below and above the dividing wall region, and metal fabric rings made of stainless steel of diameter 5 mm were installed in the dividing wall region. In separation performance measurements which were carried out with the xylene isomer mixture at a top pressure of 60 mbar, an overall separating performance of 100 theoretical plates over the entire column and about 55 theoretical plates in the dividing wall region was measured. The total number of theoretical plates present was thus about 155. The column was equipped with an oil-heated thin-film evaporator (0.1 m²) and a condenser cooled with cooling water.

Temperatures at different levels in the column and the top pressure and the pressure drop over the column were measured by means of a measurement capture system. The column possessed flow meters in the inlets and outlets, and a quantitative measurement of the reflux, which served as the control parameter for the flow temperature of the oil thermostat. This closed-loop control ensured a constant reflux rate, which also established a constant pressure difference. The division of the amount of liquid above the dividing wall between feed section and withdrawal section of the dividing wall was achieved by means of a swivel funnel on a time cycle.

At a height of 136 cm from the feed section of the dividing wall, 461 g/h of a liquid mixture which had been preheated to 110° C. and consisted of 48.7 GC area % of neral, 47.8 GC area % of geranial and 1.4 GC area % of other citral isomers were fed to the column. The column was operated at top pressure 10 mbar and a reflux of 2.5 kg/h. This established a pressure drop of about 34 mbar (±1 mbar). At the top of the column a temperature of 82.3° C. was measured and, at the bottom, a temperature of 128.4° C. (±0.5 K). By means of balance control, the bottom draw was fixed to 240 g/h and the distillate removal to 20 g/h (±1 g/h). The reflux ratio was thus about 125:1. The liquid was divided above the dividing wall in a ratio of 1:1.1 (feed:withdrawal section). At a height of 490 cm, in the withdrawal section of the dividing wall, a gaseous side draw (f) was withdrawn and condensed in a glass condenser, from which, according to the bottom fill level, about 200 g/h of pure product were drawn off by means of a pump.

The fractions obtained were analyzed by gas chromatography with the aid of a standard GC. Gas chromatography analyses were carried out by the following methods:

25 m OV-1, ID.: 0.32 mm, FD.: 0.31 µm; 50° C./2 min—10° C./min to 150° C., 5 min—20° C./min to 280° C./15 min; $t_R$ (citral isomer III): 10.4 min; $t_R$ (citral isomer IV): 10.7 min; $t_R$ (citral isomer V): 11.0 min; $t_R$ (neral I): 12.3 min; $t_R$ (geranial II): 12.6 min The pure product obtained at the side draw comprised, as well as 98.5 GC area % of neral, also 0.3 GC area % of geranial and 0.65 GC area % of other citral isomers. In the bottom draw, GC analysis was used to determine 92.5 GC area % of geranial and 6.8 GC area % of neral; the distillate comprised 32.1 GC area % of neral and 39.6 GC area % of other citral isomers.

Example 2

The column described in example 1 was supplemented with a further gaseous side draw (n) in the upper combined column section (1) at a height of about 590 cm, which was again provided with a side condenser. A balance control system was used to establish a withdrawal rate of 15 g/h (±1 g/h) there.

460 g/h of a liquid mixture, preheated to 110° C., of 50.2 GC area % of neral, 47.2 GC area % of geranial and 0.9 GC area % of other citral isomers was fed to the column at a height of 136 cm to the feed section of the dividing wall. The column was operated at top pressure 10 mbar and a reflux rate of 2.5 kg/h. This established a pressure drop of about 37 mbar (±1 mbar). At the top of the column, a temperature of 68.8° C. was established, and, at the bottom, a temperature of 130.1° C. (±0.5 K). The bottom draw was fixed to 240 g/h by means of a balance control system and the distillate withdrawal was set to about 3 g/h (±1 g/h). The reflux ratio was thus from about 600 to 1200:1. The liquid was divided above the dividing wall in a ratio of 1:1.1 (feed section:withdrawal section). At a height of 490 cm, a gaseous side draw (f) was again withdrawn in the withdrawal section of the dividing wall and condensed in a glass condenser, from which, according to the bottom fill level, about 200 g/h of pure product were withdrawn by means of a pump.

The pure product obtained at the side draw (f) comprised, as well as 98.5 GC area % of neral, also 0.3 GC area % of geranial and 0.5 GC area % of other citral isomers. The top side draw comprised, as well as 55.5 GC area % of neral, 29.5 GC area % of other citral isomers. In the bottom draw, 90.3 GC area % of geranial and 8.9 GC area % of neral were determined by GC analysis; the distillate comprised only traces of neral and 48.5 GC area % of other citral isomers.

Comparative Example

In a simple glass laboratory column with an internal diameter of 50 mm, which was equipped with 6 m of Sulzer CY packing and had no dividing wall or side draw (about 90 theoretical plates), a mixture of 50.2 GC area % of neral, 47 GC area % of geranial and 1.3 GC area % of other citral isomers was distilled continuously at top pressure 5 mbar. The feed rate was 500 g/h; 250 g/h were discharged at the bottom. The pressure drop over the column was about 28 mbar at a reflux ratio of 11:1, the bottom temperature was 121° C. and the top temperature was 81° C.

At the top condenser, at about 20° C., approx. 250 g/h of a liquid distillate with a neral content of 88.1 GC area % and a geranial content of 2.7 GC area % were obtained; the content of other citral isomers in the distillate was a total of 7.0 GC area %, which leads to the conclusion of noticeable formation of these isomers under distillation conditions.

The invention claimed is:
1. A continuous process for preparing neral of the formula (I)

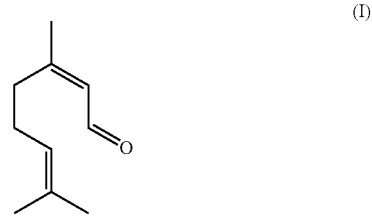

in pure form which comprises distillative separation of a neral from a substance mixture comprising neral and geranial of the formula (II)

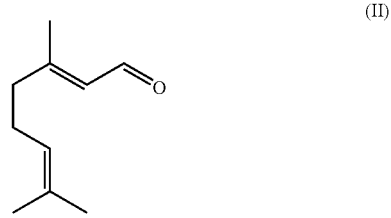

wherein the distillative separation is performed in a dividing wall column or in a connection of two distillation columns in the form of a thermal coupling with from 80 to 200 theoretical plates and one or more side draws at an absolute operating pressure of from 5 to 200 mbar, and wherein the substance mixture consists to an extent of from 30 to 70% by weight of neral, to an extent of from 70 to 30% by weight of geranial and to an extent of from 0 to 5% by weight of further components, where the percentages do not exceed 100% by weight.

2. The process according to claim 1, wherein the distillative separation is performed in such a way that the substance mixture comprising neral and geranial used is separated into in each case one or more low boiler, medium boiler and high boiler fraction(s) and neral is withdrawn in pure form as a medium boiler fraction at the one or more side draws in liquid or gaseous form.

3. The process according to claim 1, wherein the dividing wall column or the connection of two distillation columns in the form of a thermal coupling is operated at an absolute top pressure of from 10 to 40 mbar and at an absolute bottom pressure of from 20 to 50 mbar.

4. The process according to claim 1, wherein a dividing wall column is used, which has a dividing wall dividing a subregion of the column in the longitudinal direction of the column to form an upper combined column region, a lower combined column region, a feed section with rectifying section and stripping section and a withdrawal section with stripping section and rectifying section, and wherein the subregion of the column which is divided by the dividing wall and consists of subregions and or parts thereof is equipped with structured packings or random packings.

5. The process according to claim 4, wherein the substance mixture which comprises neral and geranial is fed into the middle region of the feed section, the neral is obtained in pure form as a side draw from the middle region of the withdrawal section and one or more low boiler fractions are removed from the upper combined column region and one or more high boiler fractions from the lower combined column region.

6. The process according to claim 2, wherein the distillative separation is performed in a dividing wall column comprising a lower combined column region and at least one high boiler fraction is obtained as a gaseous or liquid side draw in the lower combined column region.

7. The process according to claim 2, wherein the distillative separation is performed in a dividing wall column comprising an upper combined column region and at least one low boiler fraction is obtained as a liquid side draw in the upper combined column region.

8. The process according to claim 1 for preparing neral of the formula (I) in pure form by distillative separation of neral from substance mixtures comprising neral and geranial of the formula (II),
the distillative removal being performed in a dividing wall column which has a dividing wall in the longitudinal direction of the column to form an upper combined column region, a lower combined column region, a feed section with rectifying section and stripping section, and a withdrawal section with stripping section and rectifying section, having from 80 to 200 theoretical plates and a plurality of side draw points at an absolute operating pressure of from 5 to 200 mbar, and
neral being obtained in pure form as a side draw from the middle region of the withdrawal section and
a low boiler fraction being obtained as a liquid or gaseous side draw, from the upper combined region of the dividing wall column.

9. The process according to claim 1 for preparing neral of the formula (I) in pure form by distillative separation of neral from substance mixtures comprising neral and geranial of the formula (II),
the distillative removal being performed in a dividing wall column which has a dividing wall in the longitudinal direction of the column to form an upper combined column region, a lower combined column region, a feed section with rectifying section and stripping section, and a withdrawal section with stripping section and rectifying section, having from 80 to 200 theoretical plates and from 2 to 4 side draw points at an absolute operating pressure of from 5 to 200 mbar, and
neral being obtained in pure form as a side draw from the middle region of the withdrawal section and
a low boiler fraction being obtained as a liquid side draw from the upper combined region of the dividing wall column.

10. The process according to claim 1 for preparing neral of the formula (I) in pure form by distillative separation of neral from substance mixtures comprising neral and geranial of the formula (II),
the distillative removal being performed in a dividing wall column which has a dividing wall in the longitudinal direction of the column to form an upper combined column region, a lower combined column region, a feed section with rectifying section and stripping section, and a withdrawal section with stripping section and rectifying section, having from 80 to 200 theoretical plates and from 2 to 3 side draw points at an absolute operating pressure of from 5 to 200 mbar, and
neral being obtained in pure form as a side draw from the middle region of the withdrawal section and
a low boiler fraction being obtained as a liquid side draw from the upper combined region of the dividing wall column.

11. The process according to claim 1, wherein the dividing wall column or connection of two distillation columns in the form of a thermal coupling comprises a feed point and a side draw point which, with regard to the position of the theoretical plates, are arranged at different heights in the column, by virtue of the feed point being arranged from 1 to 50 theoretical plates higher or lower than the side draw point.

12. The process according to claim 4, wherein the subregion of the column divided by the dividing wall, consisting of subregions or parts thereof, is equipped with structured packings or random packings and/or the dividing wall is configured with thermal insulation in these subregions.

13. The process according to claim 1, wherein a dividing wall column is used which comprises a lower end and a vapor stream at the lower end, the vapor stream at the lower end of the dividing wall is adjusted through the selection and/or dimensions of the separating internals and/or the incorporation of devices which generate a pressure drop such that the ratio of the vapor stream in the feed section to that of the withdrawal section is from 0.8 to 1.2.

14. The process according to claim 1, wherein the liquid effluxing from the upper combined section of the column is collected in a collecting space arranged within the column or outside the column and divided in a controlled manner by a fixed or regulable setting at the upper end of the dividing wall such that the ratio of the liquid stream to the feed section relative to that to the withdrawal section is from 0.1 to 2.0 in the case of a principally liquid feed and from 1.0 to 2 in the case of a gaseous feed.

15. The process according to claim 1, wherein a dividing wall column is used which comprises an upper end, and a distillate is withdrawn under temperature control and the control temperature used is a measurement point in a subregion of the column which is arranged from 3 to 8 theoretical plates below the upper end of the column.

16. The process according to claim 1, wherein the substance mixtures is fed to the dividing wall column or connection of two distillation columns in the form of a thermal coupling at a feed rate and a bottom product is withdrawn under quantitative control depending on the feed rate and wherein the one or more side draws is withdrawn under level control, the control parameter used being the liquid level in the of the dividing wall column or connection of two distillation columns in the form of a thermal coupling.

17. The process according to claim 1, wherein the dividing wall column or connection of two distillation columns in the form of a thermal coupling comprise a bottom evaporator, a top condenser, and a column jacket; and the bottom evaporator used is a thin-film apparatus and/or the top condenser is configured as a plate apparatus and integrated into the column jacket.

* * * * *